United States Patent
Schiendzielorz (10) Patent No.: US 10,485,923 B2
(45) Date of Patent: Nov. 26, 2019

(54) PROVIDING TEMPERATURE-BASED FEEDBACK REGARDING DELIVERY OF A MEDICAMENT

(71) Applicant: Sanofi, Paris (FR)

(72) Inventor: Eva Schiendzielorz, Frankfurt am Main (DE)

(73) Assignee: Sanofi, Paris (FR)

( * ) Notice: Subject to any disclaimer, the term of this patent is extended or adjusted under 35 U.S.C. 154(b) by 27 days.

(21) Appl. No.: 15/508,569

(22) PCT Filed: Sep. 11, 2015

(86) PCT No.: PCT/EP2015/070862
§ 371 (c)(1),
(2) Date: Mar. 3, 2017

(87) PCT Pub. No.: WO2016/041867
PCT Pub. Date: Mar. 24, 2016

(65) Prior Publication Data
US 2017/0252508 A1    Sep. 7, 2017

(30) Foreign Application Priority Data
Sep. 15, 2014  (EP) ................... 14306415

(51) Int. Cl.
*A61M 5/142* (2006.01)
*A61M 5/145* (2006.01)
*A61M 5/168* (2006.01)

(52) U.S. Cl.
CPC ...... *A61M 5/14244* (2013.01); *A61M 5/1452* (2013.01); *A61M 5/168* (2013.01);
(Continued)

(58) Field of Classification Search
CPC .......... A61M 5/14244; A61M 5/14248; A61M 5/1452; A61M 5/168; A61M 2005/14268;
(Continued)

(56) References Cited

U.S. PATENT DOCUMENTS 3,985,133 A * 10/1976 Jenkins ................. A61M 5/172
   604/67
5,449,379 A *  9/1995 Hadtke .............. A61B 17/1325
   606/203
(Continued)

FOREIGN PATENT DOCUMENTS

EP         1 885 341      2/2008
WO    WO 2006/127905     11/2006
(Continued)

OTHER PUBLICATIONS

International Search Report and Written Opinion in International Application No. PCT/EP2015/070862, dated Oct. 22, 2015, 9 pages.
(Continued)

*Primary Examiner* — Manuel A Mendez
(74) *Attorney, Agent, or Firm* — Fish & Richardson P.C.

(57) ABSTRACT

A device configured to deliver a medicament to a user by injection, comprising an injection feedback apparatus configured to apply temperature-based feedback to the user regarding the delivery of the medicament.

18 Claims, 4 Drawing Sheets

(52) U.S. Cl.
CPC . *A61M 2205/364* (2013.01); *A61M 2205/368* (2013.01); *A61M 2205/3653* (2013.01); *A61M 2205/3673* (2013.01); *A61M 2205/582* (2013.01)

(58) Field of Classification Search
CPC .. A61M 2005/14284; A61M 2205/364; A61M 2205/3653; A61M 2205/3673; A61M 2205/368; A61M 2205/58; A61M 2205/582
USPC ............................................ 604/66, 113, 291
See application file for complete search history.

(56) References Cited

U.S. PATENT DOCUMENTS

| | | | | |
|---|---|---|---|---|
| 5,578,014 | A * | 11/1996 | Erez | A61F 7/10 604/192 |
| 5,879,378 | A * | 3/1999 | Usui | A61F 7/034 126/263.02 |
| 6,362,740 | B1 * | 3/2002 | Jung | G08B 3/1041 340/573.1 |
| 7,981,102 | B2 * | 7/2011 | Patel | A61M 5/1413 604/500 |
| 8,255,004 | B2 * | 8/2012 | Huang | H04M 19/041 455/456.1 |
| 10,143,800 | B2 * | 12/2018 | Ledford | A61M 5/14 |
| 2003/0100040 | A1 * | 5/2003 | Bonnecaze | A61B 5/0031 435/14 |
| 2006/0271020 | A1 | 11/2006 | Huang et al. | |
| 2011/0046547 | A1 | 2/2011 | Mantle | |
| 2013/0021234 | A1 | 1/2013 | Umminger et al. | |
| 2013/0135214 | A1 | 5/2013 | Li et al. | |
| 2014/0200510 | A1 | 7/2014 | Agard et al. | |

FOREIGN PATENT DOCUMENTS

| | | |
|---|---|---|
| WO | WO 2006/134153 | 12/2006 |
| WO | WO 2013/152323 | 10/2013 |
| WO | WO 2014/026977 | 2/2014 |

OTHER PUBLICATIONS

International Preliminary Report on Patentability in International Application No. PCT/EP2015/070862, dated Mar. 21, 2017, 7 pages.

* cited by examiner

PROVIDING TEMPERATURE-BASED FEEDBACK REGARDING DELIVERY OF A MEDICAMENT

CROSS-REFERENCE TO RELATED APPLICATIONS

This application is a U.S. national stage application under 35 USC § 371 of International Application No. PCT/EP2015/070862, filed on Sep. 11, 2015, which claims priority to European Patent Application No. 14306415.2, filed on Sep. 15, 2014, the entire contents of which are incorporated herein by reference.

FIELD

This specification relates to providing feedback to a user regarding delivery of a medicament. Particularly, but not exclusively, the specification relates to a feedback apparatus which applies temperature-based feedback to a user regarding delivery of a medicament.

BACKGROUND

Wearable devices for delivering medicament to a patient are sometimes worn by the patient for a significant length of time in order to allow the medicament to be delivered at a desired rate or over a desired time period. An example of this type of wearable device is a bolus injector, which is typically worn like a patch against the skin. A bolus injector generally carries out automated subcutaneous delivery of relatively large volumes of liquid medicament to the patient, such as at least 1 ml. The delivery of the medicament can last for several minutes or hours. Such high capacity bolus injector devices can be called large volume devices (LVDs).

After the delivery of the medicament has been completed, the patient must remove the device from his or her body at some later time.

SUMMARY

In certain aspects, there is provided a device configured to deliver a medicament to a user by injection, comprising an injection feedback apparatus configured to apply temperature-based feedback to the user regarding the delivery of the medicament.

Temperature based feedback may provide feedback about the injection in a way which is discreet and can be intuitively understood by the user of the wearable device.

The feedback apparatus may be configured to apply the temperature-based feedback to skin tissue of the user by causing thermal energy to be applied to, or removed from, the skin tissue of the user.

Applying temperature based feedback to the skin tissue of the user may allow the feedback to be delivered in a direct and discreet manner, for example under the clothing of the user.

The feedback apparatus may be configured to heat or cool the skin tissue by changing a temperature of a patient interface element.

The patient interface element may help to provide the feedback in comfortable and/or thermally efficient manner, for example by contact with the skin tissue.

The feedback apparatus may be configured to change the temperature of the patient interface element by a predetermined amount.

The predetermined amount by which the temperature of the interface element is changed may be appropriate to allow the user to easily perceive the change in temperature and thus be aware of the feedback. If the change is an increase in temperature, it may be insufficient to denature the skin tissue of the user. An example of the predetermined amount is +/−5° C. A maximum temperature may be approximately 42° C.

The feedback apparatus may be configured to vary the temperature of the patient interface element over a predetermined time period.

The length of the period may be chosen to allow the patient to easily perceive the variation. An example is less than one minute.

The feedback apparatus may be configured to provide the temperature-based feedback in response to a trigger event associated with the delivery of the medicament.

This may allow the feedback apparatus to indicate specific events to the user, such as the completion of an injection of a dose of medicament. This may increase the quality of the feedback for the user.

The feedback apparatus may be configured to apply different temperatures to the skin tissue in response to different trigger events.

This may allow the feedback apparatus to provide multiple types of information to the user, for example by applying different temperatures to the skin tissue. This may be advantageous in that the range of feedback given to the user may be increased.

A trigger event may be the completion of an injection of medicament from the device.

This may allow the device to inform the user that the device can be safely removed from the body.

The feedback apparatus may comprise a Peltier element configured to control the temperature of a localized region of the skin tissue of the user to provide the temperature-based feedback.

The Peltier element may allow accurate temperature control of the skin tissue and thus high quality and differentiable feedback for the user.

The feedback apparatus may comprise an electrically resistive heating element or infra-red heating element to cause heating of the skin tissue of the user.

This may allow the device to cause rapid heating of the skin tissue and thus enable the device to provide the feedback quickly in response to a trigger event.

The feedback apparatus may be configured to initiate an endothermic or exothermic chemical reaction to cause cooling or heating of the skin tissue of the user.

This may allow the device to cause rapid heating or cooling of the skin tissue and thus enable the device to provide the feedback quickly in response to a trigger event.

The device may comprise a contact region to be worn against the skin of the user and the feedback apparatus may be arranged to apply the temperature-based feedback to skin tissue beneath the contact region.

Application of the feedback to the area of skin beneath the contact region may make it easier for the user to associate the feedback with the device and hence the injection.

The device may be configured to apply the feedback automatically in response to a patient-initiated trigger to deliver the medicament.

In this way, the feedback process may be initiated in response to first activation of the device, or some other trigger, and can thereafter proceed automatically without any separate inputs from the user. This may increase the usability of the device.

The device may be a bolus Injector device.

The device may be wearable.

The feedback apparatus may be configured to initiate a compression or expansion of gas to cause cooling or heating of the skin tissue of the user.

This may allow the device to cause rapid heating or cooling of the skin tissue and thus enable the device to provide the feedback quickly in response to a trigger event.

The device may comprise a timing element to trigger application of the temperature-based feedback to the user.

This may allow the feedback apparatus to operate without being controlled by a controller, such as a microcontroller. This may reduce the cost of producing the device.

The device may be configured to apply the feedback by allowing the skin tissue of the patient to cool naturally following a period of heating by the feedback apparatus.

This aspect of the device may allow the user to perceive the feedback in a natural way.

In certain aspects, there is provided a system comprising the device and a reservoir of medicament to be delivered into the user by injection.

In certain aspects, there is provided a method of providing feedback to a user of a device configured to deliver a medicament to the user by injection, comprising applying temperature-based feedback to the user.

BRIEF DESCRIPTION OF THE FIGURES

For the purpose of example only, embodiments are described below with reference to the accompanying figures in which.

DETAILED DESCRIPTION

A wearable fluid delivery device for delivering fluid medicament to a patient is described below. The device comprises a reservoir for storing a quantity of medicament and a dispensing interface for delivering the medicament to the patient. The device is configured to deliver the medicament from the dispensing interface by injection and to apply temperature-based feedback to the patient regarding the injection. For example, the patient can be informed of when to remove the device, or when to attend to the device for another reason, by the temperature-based feedback. The injection and the feedback are provided whilst the device is being worn against the patient's skin.

The device is described below in the context of a bolus injector, but it will be appreciated that it could alternatively be another type of Large Volume Device (LVD). Referring to an exemplary embodiment shown in FIG. 1, the device 1 comprises a protective housing 2 in which the reservoir of medicament 3 and the dispensing interface 4 are located together with other components of the device 1. The housing 2 is formed from moulded plastics or another suitable material. The reservoir of medicament 3 is provided in a capsule 5, which may contain a single dose of the medicament. The capsule 5 is formed of inert material such as glass and is secured inside an internal cavity of the housing 2. The capsule 5 may be replaceable to allow re-use of the device 1. Alternatively, the capsule 5 may be non-replaceable in the device 1 so that, once the contents of the capsule 5 has been exhausted, the device 1 can no longer be used to deliver medicament and must be disposed of. This single-use nature of the device 1 facilitates ease of operation and improves safety by ensuring that a patient cannot mistakenly install an incorrect replacement capsule.

Figure 1:
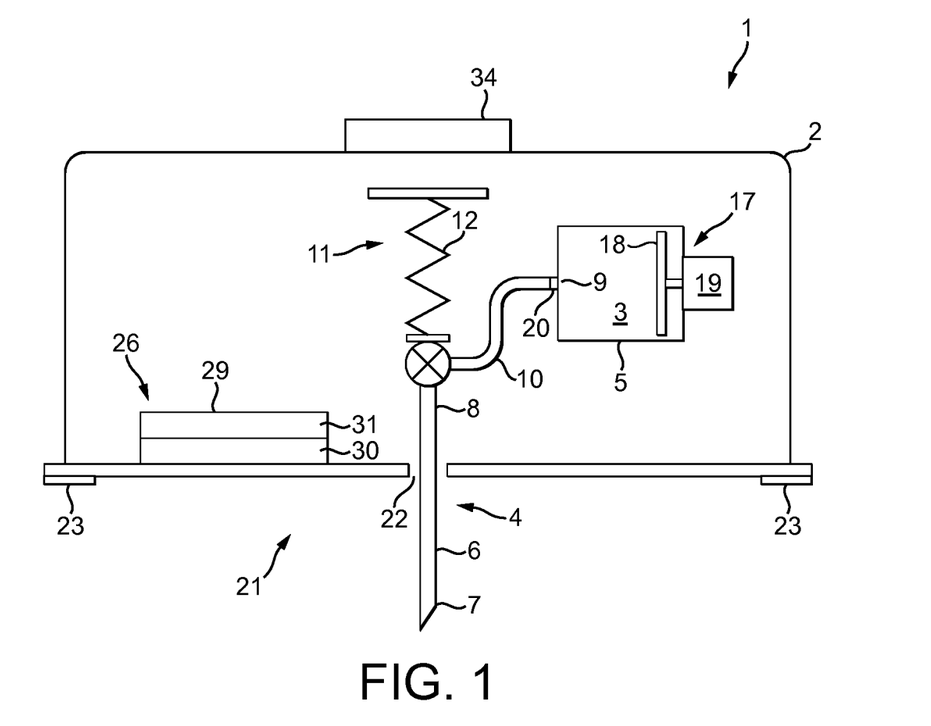
FIG. 1 is a schematic illustration of a wearable device for delivering medicament to a user by injection and applying temperature-based feedback to the user regarding the injection.

The dispensing interface 4 comprises an injection element for injection of the medicament from the device 1 into the patient. The injection element is explained below in the context of a cannula 6, as illustrated in FIG. 1, although it will be appreciated that other types of injection element could alternatively be used. Examples of alternative injection elements are discussed further below.

The cannula 6 comprises a distal end 7, which during use protrudes through the housing 2 of the device 1 into the body tissue of the patient. The cannula 6 also comprises a proximal end 8, which is arranged to receive medicament from the reservoir 3 referred to above. For example, an opening 9 in the form of an exit port in the capsule 5 may be connected to the proximal end 8 of the cannula 6 by a conduit 10 so that fluid medicament can flow from the capsule 5 into the cannula 6.

The cannula 6 may be controllably extendable and/or retractable through the exterior of the housing 2 in order to allow it to be safely stowed in the housing 2 when not in use. The device 1 may contain a user-operable actuator 11 to facilitate this. The actuator 11 is configured to cause movement of the cannula 6 relative to the housing 2 of the device 1 in order to extend and/or retract the cannula 6. An example is an actuator 11 that comprises a sprung element 12 and a switch 13 for releasing the sprung element 12. Upon release by the switch 13, the sprung element 12 may be configured to automatically extend and thereby drive the cannula 6 partially out of the housing 2 into an injection position. The actuator 11 may be electrically powered. For example, the switch 13 for releasing the sprung element 12 referred to above may be electrically powered. Electrical power may also be used to retract the sprung element 12 back to its original non-extended position, thereby also withdrawing the cannula 6. For this purpose, the actuator 11 may comprise an electrical motor 14 and a suitable drive mechanism coupled to the sprung element 12. The electrical power may be provided by a battery 15 or other power source in the device 1, which may be rechargeable.

In particular, the battery 15 may be rechargeable if the configuration of the device 1 is such that the capsule 5 of medicament is replaceable. In this type of configuration, the device 1 comprises a sterile part and a non-sterile part. The sterile part of the device 1 is replaceable and comprises the replaceable capsule 5. The non-sterile part of the device 1 is reusable and comprises reusable elements of the device 1. The elements in the non-sterile part may include, for example, a rechargeable battery 15. In general, the non-sterile part includes elements that do not need to be sterile for safe operation of the device 1 and can be safely reused. It will be appreciated, however, that there is no requirement for the elements that do not need to be sterile to be confined exclusively to the non-sterile part of the device 1. For example, it is possible for the battery 15 to be included with other replaceable elements in the sterile part of the device 1. In this configuration, the battery 15 is non-rechargeable since it is replaced each time the capsule 5 is replaced.

As will be explained in more detail below, the device 1 may comprise an electronic controller 16 which is configured to control operation of the actuator 11 and/or other elements of the device 1.

The electronic controller 16 comprises a processor and a memory and may, for example, comprise an electronic microcontroller which is communicatively coupled to the actuator 11 and/or other elements of the device 1 using a system bus (not shown). The switch 13, motor 14, battery 15 and controller 16 are shown in the block diagram of the device 1 in FIG. 2, but are not shown in FIG. 1.

The distal end 7 of the cannula 6 may be sharpened to facilitate its insertion into the body tissue of the patient. Alternatively, the dispensing interface 4 may also comprise a separate needle (not shown) for aiding the insertion of the distal end 7 of the cannula 6 into the body tissue. In this case, the cannula and the needle may together form a trocar. The needle may be controllably extendable and/or retractable from the housing 2 of the device 1 in a similar manner to the cannula 6 discussed above. The needle is configured to pierce the skin of the patient in order to allow the cannula 6 to move into the body tissue. The needle may, for example, be arranged to extend through the centre of the cannula 6. Once the skin has been pierced, the device 1 is configured to retract the needle back into the housing 2 before delivery of the medicament. In the case that the device 1 comprises a separate needle of the type described above, the device 1 may comprise an actuator similar to the one previously discussed in relation to the cannula 6 to facilitate the extension and retraction of the needle.

Another alternative is for the medicament to be delivered through the needle itself. In this case, the needle has properties which are similar to those of conventional injection needles. A proximal end of the needle is connected to the medicament reservoir 3 in a similar manner to the cannula 6 discussed above so that fluid medicament can flow through the needle into the body tissue of the patient. If the device 1 is configured in this manner, the cannula 6 may be omitted from the dispensing interface 4.

The flow of medicament into the cannula 6, or other injection element, is controlled by a flow control apparatus 17. As illustrated in FIG. 1, the flow control element may comprise a piston 18 which is moveable through the capsule 5 from one end to the other to drive medicament out of the capsule 5 through the opening 9 referred to above. A suitable drive mechanism (not shown) is mechanically coupled to the piston 18 and is operable to cause the piston 18 to move through the capsule 5. Movement of the piston 18 may be electrically powered. For example, an electric motor 19 may be connected to the drive mechanism. The electric motor 19 is powered by a power source in the device 1, such as the battery 15 referred to previously.

Additionally or alternatively, the flow control apparatus 17 may comprise a seal 20 at the opening 9 in the capsule 5 to prevent medicament from flowing out of the capsule 5 before it is intended that it should do so. The seal 20 is breakable, or openable in some other way, to allow medicament to move from the capsule 5 into the cannula 6 or other injection element via the conduit 10 referred to previously. The device 1 is configured to operate the flow control apparatus 17, for example by breaking the seal 20 and/or moving the piston 18, in response to a patient-initiated trigger, as explained below.

Figure 3:
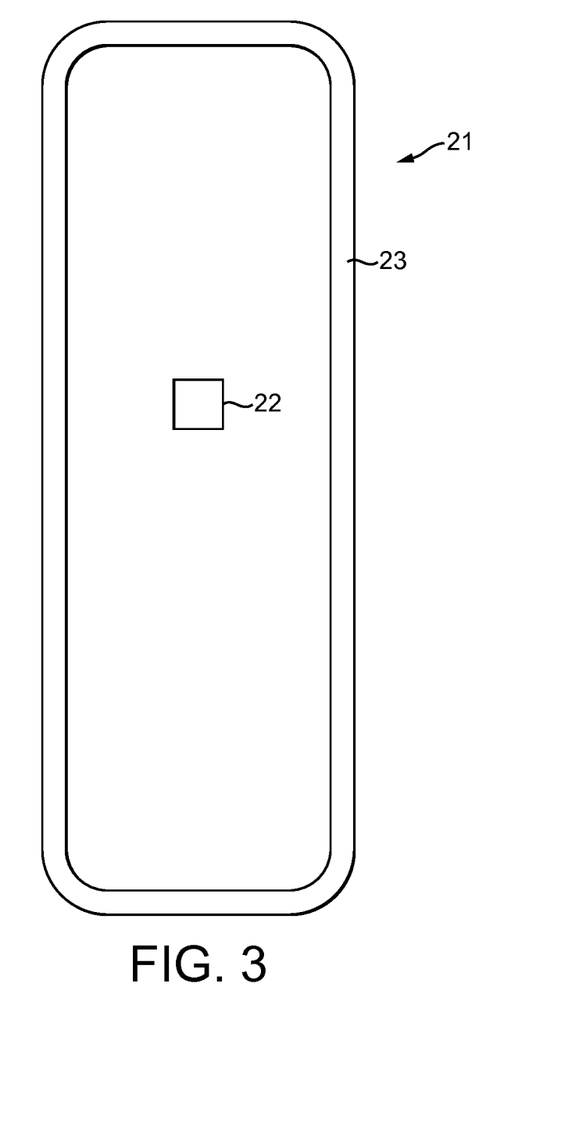
FIG. 3 is a schematic illustration of a patient contact region of a wearable device for delivering medicament to a user by injection and applying temperature-based feedback to the user regarding the injection.

Referring to FIG. 3, a contact region 21 of the housing 2 is arranged to be worn against the skin of the patient during use of the device 1. The contact region 21 may, for example, be located on a bottom face of the housing 2. The contact region 21 has geometric and tactile properties that are selected to be comfortable when worn against the skin of the patient. It is through the contact region 21 of the housing 2 that the cannula 6, or other injection element, protrudes into the body tissue of the patient during delivery of the medicament. The contact region 21 may, for example, comprise an aperture 22 through which the cannula 6 protrudes during use of the device 1. The aperture 22 is large enough to accommodate the cannula 6 and/or the separate needle referred to above, including during the extension and retraction operations previously described.

During use of the device 1, the contact region 21 is held against the skin of the patient by a fastener. The fastener is suitable for holding the contact region 21 in a stable position against the skin for a significant period of time, such as several hours, in order to ensure that the injection element is at all times maintained in a fixed position relative to the body of the patient during use of the device 1. The contact region 21 can be generally planar, or generally arcuate, and may extend across at least part of a surface of the device 1. As shown in FIGS. 1 and 3, an example of a suitable fastener is an adhesive layer 23 for temporarily adhering the contact region 21 to the skin of the patient. The adhesive layer 23 may comprise a standard biocompatible glue, as used in common adhesive bandages. In order to protect the adhesive layer 23 from damage and to prevent it from sticking to unwanted objects prior to it being attached to the skin of the patient, the contact region 21 of the device 1 also includes a protective covering (not shown) which overlies the adhesive layer 23. The protective covering is selectively removable from the contact region 21 in order to expose the adhesive layer 23 before use of the device 1, for example by peeling the covering away from the adhesive layer 23.

The device 1 also comprises a feedback apparatus 25 for providing feedback to the patient regarding the delivery of the medicament. The feedback apparatus 25 is configured to apply feedback to the body of the patient in the form of localised heating or cooling of the patient's body tissue. The degree of heating or cooling is sufficient for it to be easily perceived by the patient, as explained below. The contact region 21 and the delivery interface 4 may aid in this feedback process by being shaped and sized to facilitate high efficiency transfer of thermal energy between the feedback apparatus 25 and the body of the patient.

The feedback apparatus 25 comprises a temperature control apparatus 26 which is configured to cause heat energy to transfer into or out of the body of the patient whilst the patient is wearing the device 1. The transfers of heat energy caused by the temperature control apparatus 26 may be made in response to events associated with the delivery of the medicament into the patient. The rate at which the heat energy is caused to transfer into or out of the body of the patient following one or more of these events may be relatively rapid so that the feedback apparatus 25 can provide the patient with a sharp indication of the event. The feedback apparatus 25 may, for example, be configured to indicate an event by causing a relatively rapid increase or decrease in the temperature of the patient's skin. The temperature increase or decrease may be provided in the form of a temperature peak, in the sense that the feedback apparatus 25 causes the temperature of the skin to increase or decrease before shortly afterwards causing the temperature of the skin to decrease or increase (respectively).

The changes in the temperature of the patient's skin may be caused by the feedback apparatus 25 in either an active manner or a passive manner. For example, as described below, the feedback apparatus 25 may be configured to actively change the temperature of the patient's skin by actively heating or cooling the skin using the temperature control apparatus 26. Alternatively, the feedback apparatus 25 may be configured to change the temperature of the patient's skin by ceasing to actively heat or cool the skin. This causes a temperature change by allowing the temperature of the skin to equalize with its surroundings in a natural way.

An example of a temperature change that may be effected by the feedback apparatus 25 is a change to the temperature of the patient's skin of between approximately 2° C. and approximately 5° C. The change may be effected in a period of less than one minute, such as less than 30 seconds, or less than ten seconds. A maximum temperature to which the patient's skin may be heated is 42° C. This prevents the feedback apparatus 25 denaturing the skin of the patient.

An example of an event that may trigger the feedback apparatus 25 to cause a patient-perceivable change in the temperature of the patient's skin tissue is the completion of a medicament injection process. In particular, the device 1 may be configured to detect when a dose of medicament has been completely injected through the cannula 6 or other injection element into the patient. The feedback apparatus 25 includes one or more suitable sensors for detecting this and feeding indicative signals back the electronic controller 16 referred to previously.

For example, the feedback apparatus 25 may include a piston position sensor 27 which is configured to detect when the piston 18 described above has moved a predetermined distance along the capsule 5. The sensor 27 may be an optical sensor, although any suitable sensor may be used. The predetermined distance is indicative of one dose of medicament having been forced out of the capsule 5 through the opening 9 into the conduit 10. If the capsule 5 initially contains multiple doses of the medicament, then the predetermined distance corresponds to a partial length of the capsule 5. If the capsule 5 contains only a single dose of medicament, the predetermined distance may correspond to the full length of the capsule 5. Upon sensing that the piston 18 has travelled the predetermined distance, the piston position sensor 27 is configured to generate a signal that indicates that a dose of medicament has been expelled from the capsule 5.

The feedback apparatus 25 may additionally or alternatively comprise a sensor 28 which is configured to detect that a predetermined volume of medicament has passed out of the capsule 5 through the opening 9 referred to previously. The sensor 28 may for example be located in the opening 9 or in the conduit 10 to which the opening 9 is connected. A suitable sensor 28 is a medicament flow sensor. The sensor 28 may operate by detecting that a flow of medicament through the conduit 10 into the cannula 6 has ceased, thereby indicating that a pre-set dose of medicament has been expelled from the capsule 5 by the piston 18. Upon sensing that the dose of medicament has passed through the conduit 10, the flow sensor 28 is configured to generate a signal that indicates that the dose of medicament has been expelled from the capsule 5 into the cannula 6.

It will be appreciated that the signals from the sensors 27, 28 are indicative of the status of the delivery device 1 and, in particular, the progress of the injection of the medicament into the body tissue of the patient. The status of the delivery device 1 may be determined not only from the sensors described above, but also from other types of sensors (not shown) which detect events indicative of the status of the delivery device 1. An example of such a sensor is a position sensor configured to monitor the position of the cannula 6 or other injection element. This sensor is configured to report to the controller 16 when the cannula 6 or other injection element is extended from, or retracted into, the housing 2 and, in doing so, indicates the start and end of the delivery of the medicament into the patient.

Figure 2:
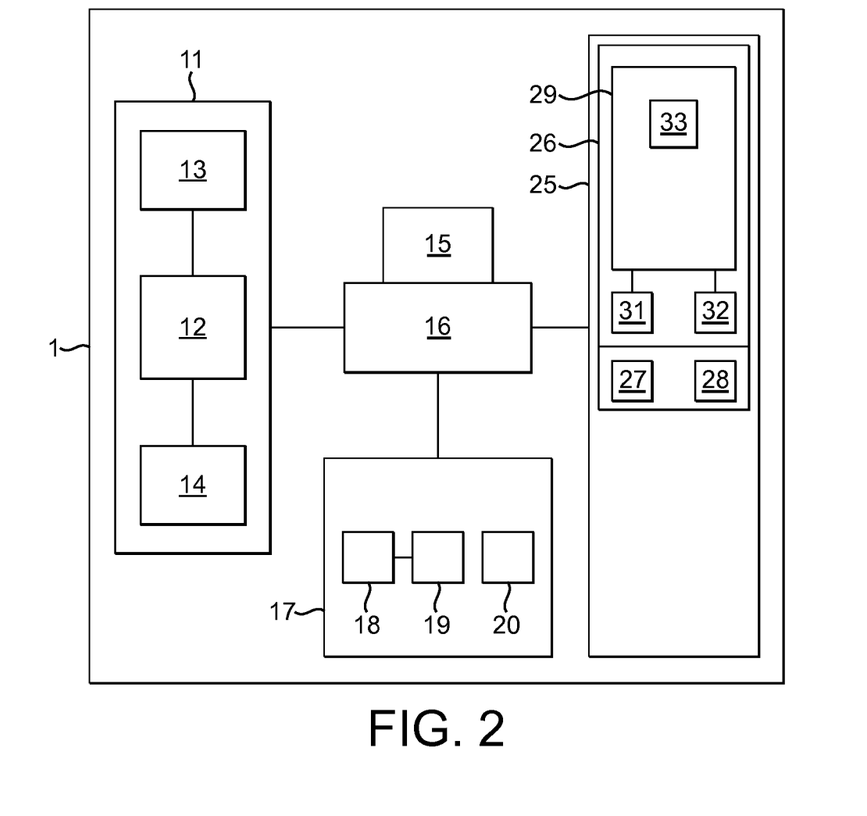
FIG. 2 is a block diagram of a wearable device for delivering medicament to a user by injection and applying temperature-based feedback to the user regarding the injection.

Signals generated by sensors 27, 28 referred to above in the feedback apparatus 25 are forwarded to the controller 16 of the device 1 via a communication coupling, which may comprise the system bus referred to previously. The controller 16 uses the signals to determine events associated with the delivery of the medicament, such as when the delivery of a dose of medicament has been completed by the dispensing interface 4. For example, the controller 16 may be configured to determine the end of the medicament delivery process from a signal indicative of the retraction of the cannula 6 or other injection element into the housing 2.

The controller 16 may make the determination of an event by analysis of the signals from the sensor(s) referred to above together with information stored in its inbuilt memory. For example, the controller 16 may contain pre-stored data which indicates the length of time taken for a dose of the medicament to be delivered through the cannula 6 following an indication from the feedback apparatus 25 that the dose of medicament has been expelled from the capsule 5. The controller 16 uses this information to calculate when the delivery of the medicament will be complete.

Another alternative is for the feedback apparatus 25 to determine events associated with the delivery of the medicament using a timing element, such as a mechanical timer. The timing element may be a count-down timer. The elapse of a count-down period of the timing element may indicate that an event has occurred. For example, the feedback apparatus 25 may comprise a timer (not shown) which is configured to count down a fixed period of time in response to the initial activation of the device 1 by the patient, or in response to the extension of the cannula 6 or other injection element from the housing 2. The duration of the count-down period is pre-set so as to be indicative of an event.

For example, the duration of the count-down period may be set to be equal to a known length of time taken to completely deliver a dose of medicament into the patient following the activation of the device 1 by the patient. The device 1 may be activated, for example, by depression of a switch 34 at the exterior of the device, as described further below. Upon elapse of the count-down period, a connection between the timer and the temperature control apparatus 26 causes the temperature control apparatus 26 to provide temperature-based feedback regarding the event indicated by the timer. The connection between the timer and temperature control apparatus 26 may be mechanical or electrical. This type of timer-based configuration may be particularly applicable if the device 1 does not comprise the central controller 16 described above.

The temperature control apparatus 26 is located in a region of the housing 2 of the device 1 which is close to the skin tissue of the patient. For example, as illustrated in FIG. 1, the temperature control apparatus 26 may be located in the contact region 21 referred to above so that it is positioned to effect a rapid transfer of heat energy between the temperature control apparatus 26 and the skin tissue of the patient.

Referring to FIG. 1, an example of a temperature control apparatus 26 comprises one or more thermoelectric heating or cooling elements, which may be provided as part of a thermoelectric heating or cooling device 29. A specific example of thermoelectric heating or cooling device is a Peltier device, which comprises one or more Peltier elements. The thermoelectric device 29 comprises a patient interface material 30 which is configured to transfer heat energy into or out of the skin tissue of the patient. This may occur either through thermally conductive contact with the patient's skin tissue or through thermal convection or conduction through a suitable intermediate heat transfer medium, as illustrated in FIG. 1. The patient interface material 30 is an electrically and thermally conductive material which is electrically connected to a different electrically and thermally conductive material 31 on the opposite side of the device 1. The thermoelectric device 29 is configured to cause an electrical current to flow across the junction between the materials 30, 31 to generate a difference in temperature between the materials 30, 31 due to the Peltier effect. Using this effect, the thermoelectric device 29 is configured to control the temperature of the patient interface material 30 to a high degree of accuracy by monitoring the temperature of the interface material 30 and applying an appropriate electrical voltage across the junction between the materials 30, 31.

Referring to FIG. 2, the temperature of the patient interface material 30 is detected by a temperature sensor 32, for example in the form of a thermistor, which is located in close proximity to the surface of the material 30. Using signals from this temperature sensor 32, the thermoelectric device 29 adjusts the voltage applied across the junction between the different materials 30, 31, and thereby the temperature of the patient interface material 30, to obtain a desired value at the sensor 32. The desired temperature of the patient interface material 30 at any given time may be communicated to the thermoelectric device 29 by the controller 16 based on pre-stored values and the information being fed to the controller 16 by the sensors 27, 28 in the feedback apparatus 25. In this way, the controller 16 is configured to respond to events such as the completion of an injection by causing the thermoelectric device 29 to change the temperature of the patient interface material 30.

The change in temperature of the patient interface surface 30 is perceived by the patient through a flow of thermal energy between the patient interface surface 30 and a localized region of the patient's body around the injection site. This informs the patient that an event associated with the injection of the medicament has recently taken place. The patient may experience either a heating or a cooling sensation, depending on the configuration of the thermoelectric device 29. Either sensation is equally possible by suitable control of the temperature of the surface of the patient interface material 30. For example, the controller 16 may be configured to respond to an event associated with the delivery of the medicament by causing the thermoelectric device 29 to cool the surface of the patient interface material 30 to a temperature which is significantly lower than the body temperature of the patient. An example is five degrees Celsius lower than the body temperature of the patient. Conversely, the controller 16 may be configured to respond to another event associated with the delivery of the medicament by causing the thermoelectric device 29 to heat the surface of the patient interface material 30 to a temperature which is significantly higher than the body temperature of the patient. An example is five degrees Celsius higher than the body temperature of the patient.

If the thermoelectric device 29 is configured to routinely cool the localized area of the patient's body by lowering the temperature of the patient interface material 30, the thermoelectric device 29 may comprise a heat sink 33 arranged to transfer the heat energy extracted from the patient interface material 30 away from the thermoelectric device 29.

In addition or as an alternative to a thermoelectric device, the temperature control apparatus 26 may comprise other heating or cooling elements or devices. An example is an element or device which is configured to heat or cool its surroundings by creating an exothermic or endothermic chemical reaction in a reaction module. Another example is an element or device which is configured to heat or cool its surroundings by compression and/or expansion of a gas, such as a heat pump. Another example is an element or device which is configured to output infra-red energy, such as an infra-red heating element. Another example is an element or device comprising an electrically resistive heating element. The elements and devices may respond to signals from the controller 16 to initiate the heating or cooling of the localized area of the patient's body in a similar manner to the thermoelectric device. It will be appreciated, however, that these alternative heating elements and devices could alternatively be triggered by a relatively simple mechanical or electrical timer of the type described previously.

In all cases, the temperature control apparatus 26 comprises an interface element through which the feedback is applied to the patient's skin. This is generally a temperature controllable element of the temperature control apparatus 26 which is located in contact with, or in close proximity to, the patient's skin during delivery of the medicament to the patient. The feedback apparatus 25 may be configured to apply different temperatures to the skin tissue in response to different trigger events in order to allow the patient to easily differentiate between different types of event.

The device 1 is configured to begin delivery of the medicament to the patient in response to a user-initiated trigger. For example, as shown in FIG. 1, the device 1 may comprise a user actuatable element which is located on the exterior of the housing 2 and which the user can operate to cause the device 1 to begin delivery of the medicament. The actuatable element is described below in the context of an electrical switch 34. The switch 34 may be relatively simple to operate in order to improve the usability of the device 1 for the patient. An example is a push-button switch or similar.

Figure 4:
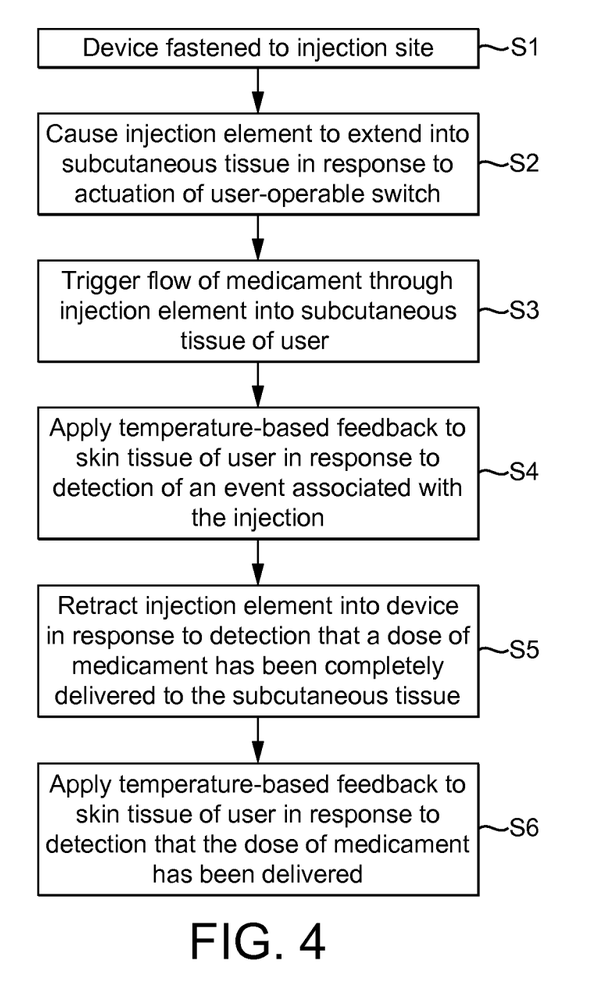
FIG. 4 is a flow diagram of a method of providing temperature-based feedback to user of a wearable device for delivering medicament by injection.

An example of a medicament injection and temperature-based feedback process is described below with respect to FIG. 4. In a first step S1, the patient fastens the contact region 21 of the device 1 to an injection site on his or her body. The patient may, for example, peel the protective covering away from the adhesive layer 23 and press the adhesive layer 23 against his or her skin to adhere the device 1 to the injection site.

In a second step S2, the patient actuates the switch 34 to begin delivery of the medicament. In response to the switch 34 being actuated, the device 1 is configured to cause the injection element to extend through the aperture 22 in the housing 2 and into the body tissue of the patient. For example, the controller 16 may be configured to receive an indication that the switch 34 has been actuated and, in response, to cause the actuator 11 to move the cannula 6 through the aperture 22 in the housing 2 into the subcutaneous tissue of the patient in the manner previously described. The device 1 may optionally comprise a sensor (not shown) that is configured to detect and report to the controller 16 when the cannula 6 has been fully extended through the aperture 22 in the housing 2 and is in position to inject the medicament into the body tissue.

In a third step S3, in response to the full extension of the cannula 6 into the patient, the controller 16 triggers a flow of medicament through the opening 7 in the capsule 5 and into the proximal end 8 of the cannula 6. For example, the controller 16 may cause power to be supplied from the battery 15 to the electric motor 19 coupled to the piston 18 in the capsule 5. The electric motor 19 drives movement of the piston 18 through the capsule 5 to expel a dose of medicament through the opening 9 in the far end of the capsule 5. If the flow control apparatus 17 comprises a seal 20 at the opening 9 of the capsule 5, this seal 20 is broken to allow the fluid medicament to be released into the conduit 10. The seal 20 may be broken by fluid pressure in the capsule 5 caused by movement of the piston 18 or may be broken by some other means, such as an actuator (not shown) which moves in response to a signal from the controller 16 to pierce the seal 20.

The device 1 is configured to deliver the dose of medicament in a manner and at a rate which is preset. For example, the dose may be administered to the patient in a continuous way at a pre-set rate. Alternatively, the dose may be administered to the patient in a plurality of discrete portions over a pre-set time period, or in any other manner, by appropriate movements of the piston 18. The manner and rate of delivery may be dictated by the controller 16

In a fourth step S4, the feedback apparatus 25 applies temperature-based feedback to the body of the patient to indicate events that are associated with the delivery of the medicament. An advantage of the temperature-based feedback that is applied by the feedback apparatus 25 is that the feedback is provided to the patient in a highly discreet manner. No person other than the patient will perceive the feedback. The patient may therefore wear the device 1 and be kept informed of the progress of the injection without any other person being aware. Another advantage of temperature-based feedback is that the patient is able to understand the feedback in an intuitive manner. A temperature change is a very natural way of receiving feedback and so the feedback apparatus 25 provides a benefit in terms of improving the ease of use of the device 1 for the patient. Humans react instinctively to hot and cold sensations on their skin. By controlling the temperature of the skin appropriately, the device 1 can provide feedback to the patient without the patient first needing to learn how the feedback will be given by the device 1. For example, the device 1 may be configured to deliver a warm sensation to the skin during an injection to indicate that all is progressing normally with the injection. This may be followed by an increase or decrease in the temperature of the skin to indicate an event such as the end of the injection. The change in temperature may be slightly uncomfortable for the patient, so that it is clearly perceived as indicating an event.

In a fifth step S5, the controller 16 is configured to cause the actuator 11 to retract the cannula 6 out of the body tissue of the patient to end the medicament delivery process.

In a sixth step S6, the feedback apparatus 25 applies further temperature-based feedback to the body of the patient to indicate that the medicament delivery process has been completed and therefore that the patient may unfasten the device 1 from his or her body.

It will be appreciated that the alternatives described can be used either singly or in combination.

Although the device 1 has been described in terms of comprising an automatically extending/retracting injection element, it will be appreciated that the injection element may be fixed so that it permanently protrudes through the housing. In these circumstances the injection element may be protected by a removable guard to minimise any danger of the element being damaged, or accidentally damaging something else, before use of the device. It will also be appreciated that in these circumstances the injection element is generally introduced into the patient's body tissue as the device is placed against the patient's skin, rather than as a subsequent step as described above. The injection element may comprise the cannula 6 described above or may comprise a needle. As indicated above, in one example the injection element comprises a trocar (which does not have a bore) of a cannula arrangement which leaves a flexible tube in the tissue of the user but does not leave the needle in the user during the medicament delivery.

The device 1 is described above as being configured to deliver the medicament subcutaneously. However, it may instead be configured for intradermal injection, for instance using a microneedle, or for injection in some other manner.

The bolus injector device may be of the type known as a Large Volume Device (LVD). An LVD injection device is configured to dispense a relatively large dose of medicament, in particular at least 1 ml and typically up to 2.5 ml, but possibly up to 10 ml.

The bolus injector device is configured to deliver a bolus of the respective medicament to bring a volume of the medicament into a patient's body within a predetermined time. The injection rate, however, may not be critical, i.e. tight control may not be necessary. However, there may be an upper (physiological) limit to the delivery rate in order to avoid damage to the tissue surrounding the delivery site. The time taken to deliver a bolus dose of medicament may be between a few minutes and many hours depending on a number of factors including the quantity (volume) of medicament, the viscosity of the medicament and the nature of the injection site at which the injection device is intended to be used.

From a user or Health Care Professional perspective, it is desirable for an injection device to be configured to minimally impact the patient's lifestyle and schedule, providing the patient with minimal reminder of his or her disease between the injections. The treatment schedule for therapies is usually intermittent, i.e. may be one injection per week, one injection every other week, or one per month. Therefore, the patient usually has no routine in dealing with his or her disease, and hence has minimal routine/experience in performing the required injections. Thus, configuration of the injection device to simplify its operation by patients is highly desirable.

Because it is intended for bolus operation, the configuration of the injection device is quite different compared to an injection device that is intended to be used for basal operation. Also, its use is quite different. For instance, a basal type insulin pump generally is relatively expensive as it includes many sophisticated diabetes specific features like programmable delivery rate profiles, bolus calculators etc. Further, the connection to the body via an infusion set allows the patient to handle and manipulate the pump in his/her field of view while the therapy is ongoing. Further, diabetes patients usually have a routine in setting-up the infusion set, connecting and operating the pump, and disconnecting the pump temporarily for events like taking a shower so not to expose the pump to water. In contrast, the bolus injector devices described above can be relatively simple and inexpensive devices. They may be provided as single-use devices, which cannot be recharged with medicament, which further reduces complexity and cost.

The actuators referred to above may comprise mechanical actuators, for example comprising one or more sprung elements. The actuators may alternatively comprise solenoids, piezo actuators, magnetic actuators or other mechanisms.

The flow of medicament through the device may controlled by one or more valves (not shown), particularly if the reservoir of medicament is pressurized in the capsule 5.

The term "drug" or "medicament", as used herein, means a pharmaceutical formulation containing at least one pharmaceutically active compound. In some embodiments, the pharmaceutically active compound can have a molecular weight up to 1500 Da or may include a peptide, a protein, a polysaccharide, a vaccine, a DNA molecule, an RNA molecule, an enzyme, an antibody or a fragment thereof, a hormone or an oligonucleotide, or a mixture of the above-mentioned pharmaceutically active compound. Various types or subtypes of compounds are also contemplated. For example, RNA may include RNAi, siRNA, or miRNA. In other embodiments, the pharmaceutically active compound can be useful for the treatment or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis or rheumatoid arthritis. In some embodiments, the pharmaceutically active compound can comprise at least one peptide for the treatment or prophylaxis of diabetes mellitus or complications associated with diabetes mellitus such as diabetic retinopathy. The pharmaceutically active compound can also comprise at least one human insulin or a human insulin analogue or derivative, glucagon-like peptide (GLP-1) or an analogue or derivative thereof, or exendin-3 or exendin-4 or an analogue or derivative of exendin-3 or exendin-4 or a pharmaceutically acceptable salt or solvate thereof.

Insulin analogues can include, for example, Gly(A21), Arg(B31), Arg(B32) human insulin; Lys(B3), Glu(B29) human insulin; Lys(B28), Pro(B29) human insulin; Asp (B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives can include, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 can include, for example, Exendin-4(1-39).

Hormones can include, for example, hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, or Goserelin.

A polysaccharide can include, for example, a glucosaminoglycane, a hyaluronic acid, a heparin, a low molecular weight heparin or an ultra low molecular weight heparin or a derivative thereof, or a sulphated, e.g. a polysulphated form of the above-mentioned polysaccharides, and/or a pharmaceutically acceptable salt thereof. An example of a pharmaceutically acceptable salt of a polysulphated low molecular weight heparin is enoxaparin sodium.

Antibodies can include generally globular plasma proteins (~150 kDa) that are also known as immunoglobulins which share a basic structure. As they can have sugar chains added to amino acid residues, they may also be classified as glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that can include four polypeptide chains; two heavy chains and two light chains connected by disulfide bonds between cysteine residues. Each heavy chain can be about 440 amino acids long; each light chain can be about 220 amino acids long. Heavy and light chains may each contain intra-chain disulfide bonds which stabilize their folding. Each chain is composed of structural domains called Ig domains. These domains typically contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of antibodies can be similar, the unique property of a given antibody is determined by the variable (V) regions, as detailed above. More specifically, variable loops, often three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is usually the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their inter-chain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H inter-chain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion. Pharmaceutically acceptable solvates are for example hydrates.

In some embodiments, medicaments of various viscosities can be injected. For example, viscosity could range from about 3 to about 50 cP. In other embodiments, viscosity could be less than about 3 cP or greater than about 50 cP. Injection can further include delivering a medicament to a sub-cutaneous, an intra-muscular, or a transdermal location within a patient's body. The medicament can be in the form of a liquid, gel, slurry, suspension, particle, powder, or other type.

Typical injection volumes can range from about 1 mL to about 10 mL. Rates of injection may be about 0.5 mL/min, about 0.2 mL/min, or about 0.1 mL/min. Such injection profiles may be generally constant in flow rate, generally continuous in duration, or both generally constant and generally continuous. These injections can also occur in a single step of administration. Such injection profiles may be referred to as bolus injections.

Delivery devices functioning with such medicaments may utilize a needle, cannula, or other injection element configured to deliver a medicament to the patient, as previously discussed. Such an injection element may, for example, have an external size or diameter of 27 G or less.

Further, the injection element could be rigid, flexible, and formed using a range of one or more materials. And in some embodiments, the injection element may include two or more components. For example, a rigid trocar may operate in conjunction with a flexible cannula as previously discussed. Initially, both the trocar and cannula may move together to pierce the skin. The trocar may then retract while the cannula remains at least partially within the target tissue. Later, the cannula may separately retract into the delivery device.

The insertion mechanism for inserting the insertion element may take any suitable form. As described above, it may be a mechanical spring based mechanism. Alternatively, the insertion element mechanism may for instance include an electric motor and a gear mechanism that causes insertion of the insertion element into the user. Alternatively, the insertion mechanism may be a gas or fluid pressure operated mechanism, in which case the needle driving energy source is either a reservoir of pressurized gas or a chemical system in which two or more chemicals are mixed together to produce gas or fluid pressure.

The invention claimed is:

1. A device configured to deliver a medicament to a user by injection, the device comprising an injection feedback apparatus configured to apply temperature-based feedback to the user regarding the delivery of the medicament, wherein the feedback apparatus is configured to provide the temperature-based feedback in response to a trigger event associated with the delivery of the medicament and wherein the trigger event is the completion of an injection of medicament from the device.

2. The device according to claim 1, wherein the feedback apparatus is configured to apply the temperature-based feedback to skin tissue of the user by causing thermal energy to be applied to, or removed from, the skin tissue of the user.

3. The device according to claim 1, wherein the feedback apparatus is configured to heat or cool skin tissue by changing a temperature of a patient interface element.

4. The device according to claim 3, wherein the feedback apparatus is configured to change the temperature of the patient interface element by a predetermined amount.

5. The device according to claim 3, wherein the feedback apparatus is configured to vary the temperature of the patient interface element over a predetermined time period.

6. The device according to claim 1, wherein the feedback apparatus is configured to apply different temperatures to skin tissue of the user in response to different trigger events.

7. The device according to claim 1, wherein the feedback apparatus comprises a Peltier element configured to control the temperature of a localized region of skin tissue of the user to provide the temperature-based feedback.

8. The device according to claim 1, wherein the feedback apparatus comprises an electrically resistive heating element or infra-red heating element to cause heating of skin tissue of the user.

9. The device according to claim 1, wherein the feedback apparatus is configured to initiate an endothermic or exothermic chemical reaction to cause cooling or heating of skin tissue of the user.

10. The device according to claim 1, wherein the device comprises a contact region to be worn against skin of the user and wherein the feedback apparatus is arranged to apply the temperature-based feedback to skin tissue of the user beneath the contact region.

11. The device according to claim 1, wherein the device is configured to apply the feedback automatically in response to a patient-initiated trigger to deliver the medicament.

12. The device according to claim 1, wherein the feedback apparatus is configured to initiate a compression or expansion of gas to cause cooling or heating of skin tissue of the user.

13. The device according to claim 1, comprising a timing element to trigger application of the temperature-based feedback to the user.

14. The device according to claim 1, wherein the feedback apparatus is configured to apply the temperature-based feedback by allowing skin tissue of the user to cool naturally following a period of heating by the feedback apparatus.

15. The device according to claim 1, wherein the device is wearable.

16. The device according to claim 1, wherein the device is a bolus injector device.

17. A system comprising:
a device configured to deliver a medicament to a user by injection, the device comprising an injection feedback apparatus configured to apply temperature-based feedback to the user regarding the delivery of the medicament, wherein the feedback apparatus is configured to provide the temperature-based feedback in response to a trigger event associated with the delivery of the medicament and wherein the trigger event is the completion of an injection of medicament from the device; and
a reservoir of the medicament to be delivered into the user by injection.

18. A method of providing feedback to a user of a device configured to deliver a medicament to the user by injection, the method comprising:
detecting that a medicament injection process has been completed by the device; and
in response to determining that the medicament injection process has been completed, applying temperature-based feedback to the user.

\* \* \* \* \*